(12) United States Patent
Bertleson et al.

(10) Patent No.: US 9,138,535 B2
(45) Date of Patent: Sep. 22, 2015

(54) HIGH PRESSURE INJECTION CATHETER SYSTEMS

(75) Inventors: Kathryn A. Bertleson, Minnetonka, MN (US); Justin M. Crank, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 375 days.

(21) Appl. No.: 13/262,553

(22) PCT Filed: Jul. 20, 2010

(86) PCT No.: PCT/US2010/042578
§ 371 (c)(1),
(2), (4) Date: Sep. 30, 2011

(87) PCT Pub. No.: WO2011/011396
PCT Pub. Date: Jan. 27, 2011

(65) Prior Publication Data
US 2012/0109050 A1   May 3, 2012

Related U.S. Application Data

(60) Provisional application No. 61/227,118, filed on Jul. 21, 2009, provisional application No. 61/226,804, filed on Jul. 20, 2009.

(51) Int. Cl.
*A61M 5/307* (2006.01)
*A61M 5/145* (2006.01)
*A61M 37/00* (2006.01)
*A61M 5/30* (2006.01)
*A61M 5/34* (2006.01)
*A61M 25/00* (2006.01)

(52) U.S. Cl.
CPC ........... *A61M 5/145* (2013.01); *A61M 25/0069* (2013.01); *A61M 37/00* (2013.01); *A61M 5/30* (2013.01); *A61M 5/348* (2013.01); *A61M 25/001* (2013.01); *A61M 2025/0079* (2013.01); *A61M 2205/502* (2013.01)

(58) Field of Classification Search
CPC . A61M 25/0069; A61M 25/007; A61M 5/30; A61M 5/3007
USPC .......... 604/211, 104, 500, 508, 27, 68, 93.01, 604/131, 151, 154, 218; 600/104; 239/87, 239/525, 390
See application file for complete search history.

(56) References Cited

U.S. PATENT DOCUMENTS

| | | | |
|---|---|---|---|
| 4,093,108 A | 6/1978 | Hein et al. | |
| 4,130,119 A | 12/1978 | Sessions et al. | |
| 4,742,817 A | 5/1988 | Kawashima et al. | |

(Continued)

FOREIGN PATENT DOCUMENTS

| | | |
|---|---|---|
| WO | WO9616606 A1 | 6/1996 |
| WO | WO 96/36381 | 11/1996 |

(Continued)

*Primary Examiner* — Laura Bouchelle
(74) *Attorney, Agent, or Firm* — Kagan Binder, PLLC (57) ABSTRACT

A needleless fluid injection system (100) including an injection console (102), an injection chamber in operative communication with the console, an injectate shaft (104) in operative communication with the console, which has an injection lumen extending from a proximal end to a distal end of the shaft, and at least one injection orifice extending through a wall of the injection lumen proximate the distal end of the shaft. The injection lumen can include a sealing cap (40) at its distal end.

12 Claims, 9 Drawing Sheets

(56) References Cited

U.S. PATENT DOCUMENTS

| | | | |
|---|---|---|---|
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A * | 8/1994 | Kaplan et al. | 604/509 |
| 5,693,016 A | 12/1997 | Gumaste et al. | |
| 5,840,062 A | 11/1998 | Gumaste et al. | |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,400,980 B1 | 6/2002 | Lemelson | |
| 6,537,205 B1 | 3/2003 | Smith | |
| 6,547,767 B1 | 4/2003 | Moein | |
| 6,641,553 B1 | 11/2003 | Chee et al. | |
| 6,905,475 B2 | 6/2005 | Hauschild et al. | |
| 7,296,308 B2 * | 11/2007 | Turner | 4/507 |
| 7,749,156 B2 | 7/2010 | Ouchi | |
| 2003/0163111 A1* | 8/2003 | Daellenbach | 604/500 |
| 2004/0030320 A1 | 2/2004 | Chee et al. | |
| 2004/0162528 A1 | 8/2004 | Horvath et al. | |
| 2005/0192530 A1 | 9/2005 | Castellano | |
| 2005/0228225 A1 | 10/2005 | Hauschild et al. | |
| 2006/0129125 A1 | 6/2006 | Copa et al. | |
| 2006/0282156 A1* | 12/2006 | Weber et al. | 623/1.19 |
| 2007/0167921 A1 | 7/2007 | Burren et al. | |
| 2007/0225554 A1 | 9/2007 | Maseda et al. | |
| 2008/0114203 A1 | 5/2008 | Crank | |
| 2008/0119784 A1 | 5/2008 | Roychowdhury | |
| 2008/0119823 A1 | 5/2008 | Crank | |
| 2009/0054872 A1 | 2/2009 | Magnuson | |
| 2009/0124974 A1 | 5/2009 | Crank et al. | |
| 2009/0312696 A1 | 12/2009 | Copa et al. | |
| 2011/0015614 A1 | 1/2011 | Rykhus, Jr. et al. | |
| 2011/0046600 A1 | 2/2011 | Crank | |

FOREIGN PATENT DOCUMENTS

| | | |
|---|---|---|
| WO | WO9736625 A1 | 10/1997 |
| WO | WO0040279 A1 | 7/2000 |
| WO | WO0066199 A1 | 11/2000 |
| WO | WO 00/72908 | 12/2000 |
| WO | WO0136029 A1 | 5/2001 |
| WO | WO 01/41656 | 6/2001 |
| WO | WO0207812 A2 | 1/2002 |
| WO | WO2004071612 A2 | 8/2004 |
| WO | WO 2005/065758 | 7/2005 |
| WO | WO2005094921 A1 | 10/2005 |
| WO | WO2006057604 A2 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

HIGH PRESSURE INJECTION CATHETER SYSTEMS

CROSS-REFERENCE TO RELATED APPLICATION

This application claims benefit from International Application No. PCT/US2010/042578, which was filed on Jul. 20, 2010, which in turns claims priority under 35 U.S.C. §119(e) to U.S. Provisional Application No. 61/227,118, filed Jul. 21, 2009, titled, "High-Pressure Injection Catheter System With Connection and Lumen Features"; and U.S. Provisional Application No. 61/226,804, filed Jul. 20, 2009, titled, "Injection Catheter and Leak Management System", the entire contents of which are both incorporated herein by reference in their entireties.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example. Needleless devices and methods for treating tissue of the urinary tract are discussed, for example, in U.S. Patent Application Publication No. 2009/0312696 (Copa et al.), and U.S. Patent Application Publication No. 2006/0129125 (Copa et al.), the entire disclosures of which are incorporated herein by reference. One particular application for needleless fluid delivery systems is for treatment of diseases of the prostate, such as prostatitis, benign prostatic hyperplasia, and prostatic carcinoma.

Needleless fluid delivery systems can include the use of a tube-like device, such as an elongated catheter tube, which is configured to provide a jet-injection of a therapeutic fluid at a desired treatment site. Generally, a needleless injector is used to deliver the therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the therapeutic fluid to a relatively high pressure in order to achieve a certain desired fluid delivery pressure at the distal end of the device.

For any injection or injected tissue, therapeutic agents are desirably delivered with minimal discomfort and procedure time, and with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery using needleless fluid delivery systems. Such procedures, systems, and components can provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention generally involves needleless fluid injection devices, systems, and methods. These devices and systems allow for targeted delivery of therapeutic fluids at desired anatomical tissue locations, such as locations in the male or female urinary tract, (e.g., bladder, bladder neck, kidney, ureters, urethra, prostate, etc.). The therapeutic fluids can include biologically active species and agents such as chemical and biochemical agents, for example. Exemplary devices can be designed to deliver fluid at various tissue locations, and can further deliver multiple different therapeutic fluids having varying material properties (e.g., viscosity). The devices can be capable of delivering precise amounts of fluid for injection at precise locations and at specific pressures that are adjustable depending on the fluid being administered to the location in the patient.

In one aspect of this invention, a needleless fluid injection system is provided that includes an injection console, an injection chamber in operative communication with the console, an injectate shaft in operative communication with the console and comprising an injection lumen extending from a proximal end to a distal end of the shaft, and at least one injection orifice extending through a wall of the injection lumen proximate the distal end of the shaft. In this embodiment, the injection lumen comprises a sealing cap that can include an internal cavity that is sized and shaped to receive an end portion of the injectate shaft. In one embodiment, the cap is secured to the injectate shaft using a swaging process.

In another aspect of the invention, a needleless fluid injection system is provided that includes an injection console, an injection chamber in operative communication with the console, an injectate shaft in operative communication with the console and comprising an injection lumen extending from a proximal end to a distal end of the shaft, at least one injection orifice extending through a wall of the injection lumen proximate the distal end of the shaft, and an injection plunger comprising an extending flange portion proximate to its proximal end, wherein the injection plunger is positioned within an inner portion of the injection chamber. The extending flange portion of the injection plunger can be engageable with the injection console, and can further include an o-ring groove and an o-ring positioned in that groove.

In another aspect of the invention, a needleless fluid injection system is provided that includes an injection console, an injection chamber in operative communication with the console, an injectate shaft in operative communication with the console and comprising an injection lumen extending from a proximal end to a distal end of the shaft, at least one injection orifice extending through a wall of the injection lumen proximate the distal end of the shaft, wherein the injection lumen is in operative communication with the injection chamber, and an intermediate connector operatively connecting a distal end of the injection chamber to the injectate shaft. In order to facilitate this attachment, the injection chamber has an extending portion extending from one end, and the intermediate connector has an internal cavity that is engageable with that extending portion of the injection chamber.

In yet another aspect of the invention, a needleless fluid injection system is provided that includes an injection console, an injection chamber in operative communication with the console, an injectate shaft in operative communication with the console and comprising an injection lumen extending from a proximal end to a distal end of the shaft, at least one injection orifice extending through a wall of the injection lumen proximate the distal end of the shaft, and a retention gasket mechanism operatively connected to the injection chamber and the injection console. The retention gasket mechanism can include a chamber receiving portion operatively connected to an end of the injection chamber and a console engagement portion engaged with a cavity of the injection console.

In another aspect of the invention, a needleless fluid injection system is provided that includes an injection console, an injection chamber in operative communication with the console, an injectate shaft in operative communication with the console and comprising an injection lumen extending from a proximal end to a distal end of the shaft, at least one injection orifice extending through a wall of the injection lumen proximate the distal end of the shaft, an injection plunger, and a connector operatively attached to the injection plunger and the injection console. In more particularity, the injection plunger can include a groove, wherein the console comprises an internal spring, and wherein the internal spring is engageable with the groove of the injection plunger.

In another aspect of the invention, a needleless fluid injection system is provided that includes an injection console, an injection chamber in operative communication with the console, an injectate shaft in operative communication with the console and comprising an injection lumen extending from a proximal end to a distal end of the shaft, at least one injection orifice extending through a wall of the injection lumen proximate the distal end of the shaft, at least one injection plunger, and a leak management system in operative engagement with the injectate shaft. In one particular embodiment, this leak management system comprises a flange extending from the injection plunger, with the flange angled away from the external body of that plunger. The system can further include a gutter extending from a surface of the injection console.

BRIEF DESCRIPTION OF THE DRAWINGS

The present invention will be further explained with reference to the appended Figures, wherein like structure is referred to by like numerals throughout the several views, and wherein.

DETAILED DESCRIPTION

The invention relates to devices and methods useful for injecting fluid into tissue for treatment. The fluid can be injected without the use of a needle and can therefore be referred to as a "needleless" fluid injection system. Needleless fluid injection systems of the invention can include one or more orifices that deliver fluid in the form of a jet or fluid stream without a needle passing into the tissue. This fluid is delivered at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets. The type of tissue injected for treatment can be any amenable tissue, such as tissue at or near the urinary tract (e.g., tissue of the prostate, kidneys, ureters, urethral tissue, bladder, or other tissues such as heart tissue).

Needleless devices of the type described herein generally include a distal end and a proximal end. As used herein, a "distal end" of a device or system refers to an end area or portion of the device or system that can be introduced internally within a patient's body during a treatment procedure. For example, the elongate shafts or catheters of the needleless injection systems of the invention generally include a distal end that is the first portion of the device that is introduced into the patient for treatment. A distal end may include functional features that operate on fluid or tissue during use, such as one or more ejection orifices, delivery heads (e.g., end effectors, nozzles, etc.) that house one or more ejection orifices, a frictional tissue holding tip, tissue tensioners, lighting or other optical features, steering features, and the like.

As used herein, a "proximal end" of an exemplary needleless device or system is the end that is opposite the distal end of that device or system. It is noted that each individual component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. That is, exemplary needleless fluid delivery devices or systems can include a proximal end that includes a console, and an elongate shaft extending from a proximal end, which is in communication with the console, to a distal end. One or more injection orifices at the distal end can be in fluid communication with the console.

An exemplary console used with systems of the invention can include a housing that connects to or is otherwise (directly or indirectly) in fluid communication with an elongate shaft or catheter tube. The console can include fluid that can be pressurized by a pressure source to cause the fluid to flow through the shaft for injection into tissue at the distal end. A device can eject fluid from one or multiple ejection orifices that can be located at the distal end of the shaft or catheter tube.

Devices, systems, and methods are described herein that can be used to inject a fluid through a surface of a tissue, penetrating without the use of a needle through the tissue surface and into the bulk of the tissue, and dispersing as particles or droplets within the tissue below the tissue surface. The fluids that are injected into tissue using systems of the invention may be referred to as an "injectate" or "injection fluid", which may be any type of fluid such as a therapeutic fluid. A fluid stream or jet of injectate can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface, disperses within the tissue, preferably as a multi-directional collection of particles (e.g., a "cloud") or droplets within the bulk of the tissue. Exemplary pressures of a fluid at a pressure chamber can be at least 200 pounds per square inch (psi), and in some embodiments can range from 300 to 5000 pounds per square inch.

Figure 1:
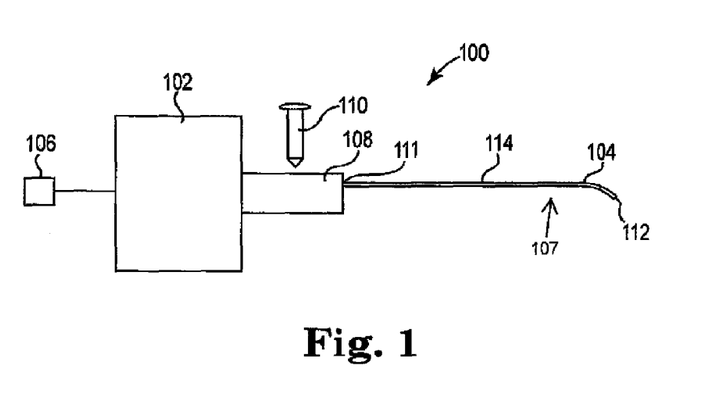
FIG. 1 is a schematic illustration of one embodiment of a needleless fluid delivery system for delivering a therapeutic fluid to a treatment location, in accordance with the invention.

Referring now to the Figures, wherein the components are labeled with like numerals throughout the several Figures, and initially to FIG. 1, one exemplary configuration of a needleless fluid delivery system 100 is schematically illustrated. Delivery system 100 generally includes an injection console 102, an injection chamber 108 in operative communication with the console 102, and a catheter tube or injectate shaft 104 that is also in operative communication with the console 102. The console 102 includes a user interface 106, which can be used for activating and controlling the activities of the various components of the delivery system 100. The user interface 106 can include an input means for selectively delivering a volume of pressurized fluid through the injection chamber 108. The user interface 106 may further include one or more actuatable devices, such as a foot petal, a hand activated controller, switches, buttons, and/or the like. It is also contemplated that the user interface 106 can include a touch-screen that is capable of receiving touch commands and may optionally include a display system for displaying information such as the mode of operation that is being used and/or certain operating parameters of the system.

Although console 102 can include a wide variety of features, any console used in the fluid delivery systems of the invention can generally include a housing, a pressure chamber, and a pressure source. The console can have any configuration, size, or design, ranging from a small, hand-held design to a relatively large floor or table-mounted console. The consoles can also include separate or separable components such as a pressure chamber or injection chamber that can be attached, used for an injection procedure, and detached and then optionally discarded or sterilized and reused. A shaft or catheter tube can also be attached to a console or a pressure chamber in a manner that facilitates separation and optional re-attachment or disposal.

With separable components, a first shaft and/or injection chamber can be attached to a console housing and used to inject a first patient and/or a first injectate, and then that shaft and/or injection chamber can be removed and discarded or sterilized. A second shaft or pressure chamber can then be attached to the same console housing to treat a second patient, or to treat the first patient with a second injectate or administer another treatment of the first injectate. The second patient or injectate can involve injection and treatment of the same type of tissue as the first patient or injectate, or of a new type of tissue than was treated in the first treatment. In this manner, separable and optionally disposable shaft or pressure chamber components of a needleless injection system can allow a console housing to be used multiple times to inject the same or different injectates to the same or different patients, and to the same or different types of body tissue, thereby providing an injection system that is flexible for use in a wide variety of situations and with a wide variety of fluids. Examples of system configurations, features and combinations of system features that can be useful according to the present description include U.S. Patent Application Publication No. 2006/0129125 (Copa et al.); U.S. Publication No. 2009/0312696, filed Jun. 27, 2008 (Copa et al.); PCT patent application Serial No. US09/06390, filed Dec. 4, 2009 (Crank et al.), titled "Devices, Systems, and Related Methods for Delivery of Fluid to Tissue"; PCT patent application Serial No. US09/06384, filed Dec. 4, 2009 (Crank), titled "Needleless Injection Device Components, Systems, and Methods"; and PCT patent application Serial No. US09/06383, filed Dec. 4, 2009 (Rykhus et al.), titled "Method and Apparatus for Compensating for Injection Media Viscosity in a Pressurized Drug Injection System", the entireties of which are all incorporated herein by reference.

The console can also include actuating features to control distal end features of the system, such as steering a distal end of a steerable shaft, actuating ejection of fluid, moving a movable or extendable injectate shaft or one or more injection orifices relative to another shaft component such as a working shaft, and may further include optional ports to connect a console housing to auxiliary devices, electronics such as controls, optic features such as a lens, fiber optic, or electronic viewing mechanism to allow viewing through an optical feature (to view a location of delivery), and an actuating mechanism or pressure source for a tissue tensioner in the form of a mechanical tissue tensioner or an inflatable balloon. One or more attachment ports can optionally facilitate attachment of a console to an external and optionally remote component such as an external or remote pressure source, vacuum source, or an external or remote fluid reservoir to supply injectate or other fluid, such as to inflate a balloon. Embodiments of consoles can include a permanent or removable injection or pressure chamber and a pressure source capable of pressurizing a fluid contained in the pressure chamber to cause the fluid to flow from the console, through a lumen in the injectate shaft, and then through an injection orifice. Examples of consoles, console features and combinations of console features that can be useful according to the present description are identified in Applicants' copending U.S. Patent Application Publication No. 2006/0129125; U.S. Publication No. 2009/0312696, filed Jun. 27, 2008 (Copa et al.); PCT patent application Serial No US09/06383; filed Dec. 4, 2009 (Rykhus et al.), titled "Method and Apparatus for Compensating for Injection Media Viscosity in a Pressurized Drug Injection System"; and PCT patent application Serial No. US09/06381, filed Dec. 4, 2009 (Crank), titled, "Devices, Systems and Methods for Delivering Fluid to Tissue", the entire disclosures of which are incorporated herein by reference.

Referring again to FIG. 1, fluid can be provided to the system 100 by a fluid supply 116, which is illustrated as a syringe that is manually activated, such as by physically pressing a plunger into a syringe barrel that is at least partially filled with fluid to push fluid from the syringe barrel. Alternatively, fluid supply 116 can have a different configuration than a syringe, and the fluid supply can be automatically or mechanically activated, such as with an electronic fluid supply controller and/or with one or more remote activation devices that can be manipulated by the user to move fluid out of a syringe barrel. In yet another alternative, the fluid supply 116 is not a syringe, but instead includes a larger fluid source, such as a reservoir or other container that holds the fluid until it is provided to the injection chamber 108. Such a container can be positioned so that the fluid is gravity fed to the injection chamber, for example, or so that the fluid can be extracted using a vacuum source, for another example. With any of the different types of fluid supplies used with the systems of the invention, it is contemplated that an exact amount of fluid to be administered can be premeasured and provided to the system until that quantity of fluid is depleted and/or a predetermined amount of fluid can be extracted from a relatively large fluid supply.

A pressure chamber or injection chamber, such as injection chamber 108, can be a type of fluid chamber for containing one or more fluids (e.g., control fluid or injectate) and/or for placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume for increasing or decreasing the volume (and correspondingly decreasing or increasing pressure) within the variable volume chamber space. Such pressure chambers can include a plunger, piston, bellows, or other mechanisms. A pressure chamber can be pressurized by a pressure source attached to the plunger, bellows, or piston, etc., such that fluid contained in the pressure chamber is ejected under pressure. This pressurized fluid can be used for priming a device and/or for ejecting fluid from an ejection orifice for injection and/or to produce a control force, for example. A pressure source may be any source of energy (e.g., mechanical, electrical, hydraulically derived, pneumatically derived, or the like) such as a spring, solenoid, compressed air, manual syringe, electric power, hydraulic, pneumatic pressure sources, or the like. A pressure chamber may be a permanent or removable (i.e., attachable and detachable) component of a console housing.

As described above, an injectate shaft extends from its proximal end, which is optionally removably connected to the console (or a component of the console such as a removable pressure chamber and/or console housing), to its distal end that can be placed in a patient during an injection procedure. The injectate shaft can be of various designs, minimally including an injection lumen to carry injectate from a proximal end of the injectate shaft to a distal end of the injectate shaft. Shafts for needleless devices as described are also described in PCT patent application Serial No. US09/06390, filed Dec. 4, 2009 (Crank et al.), titled "Devices, Systems, and Related Methods for Delivery of Fluid to Tissue"; and in PCT patent application Serial No. US09/06384, filed Dec. 4, 2009 (Crank), titled "Needleless Injection Device Components, Systems, and Methods"; the entireties of which are both incorporated herein by reference.

The injectate shaft can include structure such as sidewalls that define the injection lumen, the sidewalls being of sufficient strength to withstand operating pressures that are used to deliver injectate from the injection orifice at an elevated pressure that causes the injectate to be ejected from the injection orifice to penetrate a tissue surface and become injected into and dispersed below the tissue surface. An injectate shaft may therefore be made of a flexible material (e.g., a metal or polymeric tube) that can withstand such injection pressure, and may be prepared from materials capable of withstanding pressure of an injection (e.g., Nitinol, stainless steel, or a reinforced (e.g., braided) polymer). The injectate shaft may be fabricated using suitable high strength polymers including, for example, polyimide, polyetherimide available from General Electric under the trade name "Ultem", and linear aromatic polymers for transporting the treatment fluid and the apposing jet medium to the treatment area. In some embodiments, the injectate shaft can be reinforced through the inclusion of materials including nano-particles, clays and/or glass. In some presently contemplated embodiments, the injectate shaft can be reinforced with one or more polymers such as, for example, tubes braided with Kevlar or other high-strength polymers. The injectate shaft can be fabricated so as to have a burst strength exceeding at least about 2,000 psi. The injectate shaft can be fabricated so as to have distention properties, wherein one or more orifices or jet ports located at its distal end retains its shape and/or size without suffering swelling that can have a detrimental impact on a fluid jet used to deliver the therapeutic fluid at the treatment site.

As discussed above, a distal end of an injectate shaft includes one or multiple injection orifices for ejecting fluid within a body of a patient. An injection orifice can be any form of opening, aperture, or orifice, such as an aperture or bore in an injectate shaft sidewall, or an aperture or bore in a nozzle, end effector, injection head, or other structure in communication with an injection lumen. Injection orifices can be located at relative locations and orientations along a length or circumference of an injectate shaft distal end to result in ejection and distribution of ejected fluid in different directions (e.g., circumferentially relative to the shaft), optionally or alternately at different distances along the length of the injectate shaft. An injection orifice can be directed at any angle relative to a longitudinal axis of a shaft, such as perpendicular, angled toward a distal end, or angled toward a proximal end.

Referring again to FIG. 1, a proximal or supply end 111 of the injectate shaft 104 extends from a distal end of the injection chamber 108. The injectate shaft 104 may be permanently attached or connected to the injection chamber 108 so that the shaft 104 and chamber 108 are provided to the system as a single component. Alternatively, injectate shaft 104 may be attachable and detachable from injection chamber 108, such as with quick connection fittings, so that the injection chamber 108 and shaft 104 are provided to the system as separate components. Injectate shaft 104 further includes a delivery or distal end 112, which is generally opposite the proximal or supply end 111.

Injectate shaft 104 is a generally continuous, elongated tube, which may include multiple lumens, attachments, or other components that may extend along all or part of the length of the shaft 104. Injectate shaft 104 may further comprise a number of different configurations, such as an endoscope or other catheter configuration, for example. Alternatively, injectate shaft 104 can comprise a flexible, elongated tube 114 to allow for easy positioning of its delivery or distal end 112 within the patient. Supply or proximal end 111 of the shaft 104 can be generally configured to attach to the injection chamber 108 and can include a quick-connect style connector. Alternatively, the proximal end 111 of the shaft 104 can be permanently attached to the injection chamber 108. Either type of connection facilitates the joining of an injectate shaft, which can be subjected to relatively high pressures, to an injection chamber in a secure manner that minimizes or eliminates leakage and unintentional disconnection of components from each other. The injectate shaft can further include at least one injection orifice (shown generally by reference numeral 107 in FIG. 1) extending through a wall of the injection lumen proximate a distal end of the shaft.

A working lumen or channel can extend within the shaft 104 and can contain a fluid delivery lumen or catheter (not shown). Such a delivery lumen can be adapted to move longitudinally along the length of the shaft 104 to allow its distal end to extend from the distal tip of the shaft as an orifice extension. The high-pressure injectate is delivered to the target tissue from this delivery lumen. In particular, the injectate traverses from the fluid supply, into the working channel, and out of the fluid delivery lumen.

Figure 2:
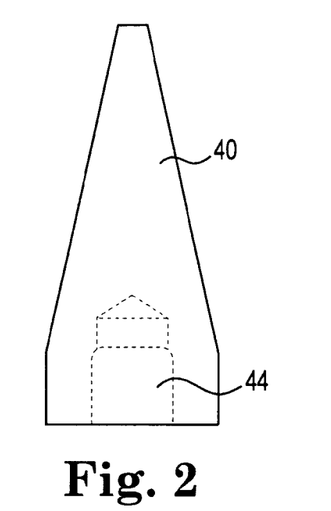
FIGS. 2 and 3 are front views of a delivery tubing cap of the invention.
Figure 3:
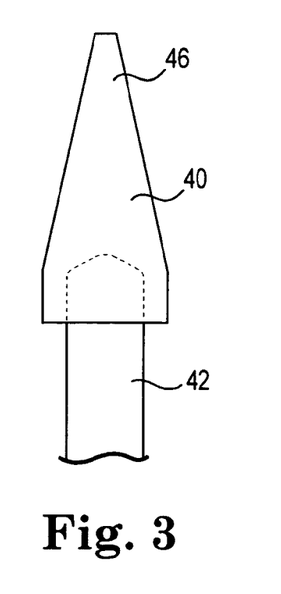

Referring now to FIGS. 2 and 3, a tapered delivery tip or cap 40 of the invention is illustrated, which is provided to create a sealed tip on the distal end of an injection tubing that is able to withstand relatively high pressures to which it can be subjected.

As such, the cap 40 can be positioned to cover the distal end of a tube or lumen 42, which can be a delivery lumen of the type described above, for example. The cap 40 can be constructed of various materials, including polymers and metals, which are chosen for their ability to withstand the associated forces, including those created by high pressure fluids (e.g., greater than about 3000 psi) and swaging.

At least a portion of the cap 40 can include a defined internal cavity 44, and in one embodiment, the cavity 44 is defined as a portion of the cap 40 opposite its distal end 46 that is hollow or otherwise adapted to receive an end portion of a delivery lumen. The cap 40 can be designed to have a relatively tight or press fit onto the outer diameter of the end of the delivery lumen when the delivery lumen is positioned within the cavity 44. In addition, the cavity 44 preferably has a predefined depth that is selected so that the location of the cap 40 relative to the delivery lumen 42 is generally at a predetermined relative location. The predefined cavity depth will also make it easier for an operator to determine the location of the cap with respect to the delivery lumen prior to performing a swaging process. In particular, the cap will slide over the distal end of an injection tubing or delivery lumen as a "cap", and the cap and tubing will be placed in a swager to lock or compress the tip onto the injection tubing. Such a swage process provides a beneficially consistent configuration, which is accurately repeatable. Various locking, sealing, snap-fit, bonding, and like configurations and techniques can be used to attach and lock the cap 40 to the end of a high-pressure lumen. Also, while the cap 40 is illustrated as having a tapered cone shape, it is contemplated that the outer shape can be different. It is further contemplated that the tip or cap can instead be attached to the injection tubing using different attachment techniques, such can be accomplished using adhesives, connectors, welding, an interference or frictional fit, and the like.

Figure 4:
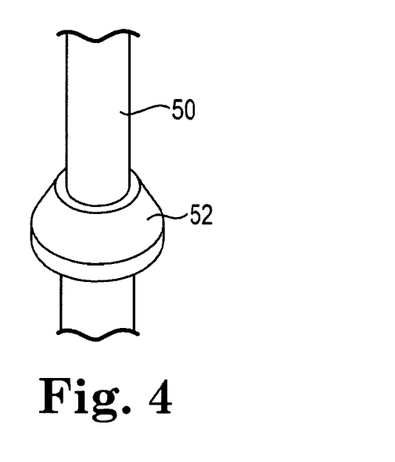
FIGS. 4 and 5 are top and bottom perspective views, respectively, of an injection plunger with an auto-loading flange mechanism for sealing with a console, in accordance with the invention.
Figures 5, 6:
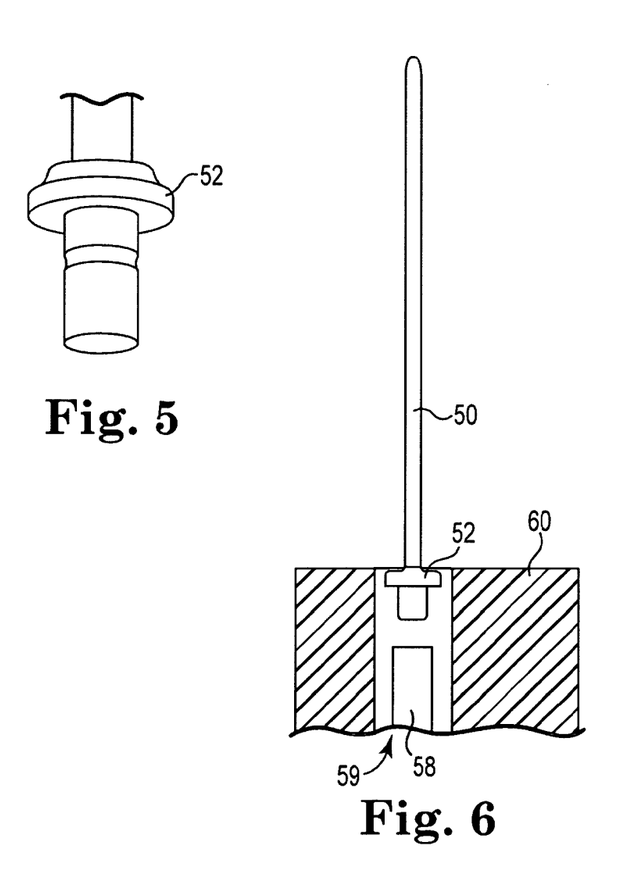
FIG. 6 is a partial cross-sectional front view of the injection plunger of FIGS. 4 and 5, as it can be seated with an exemplary console.

Referring now to FIGS. 4-6, a portion of an embodiment of an injection device or catheter system is shown, illustrating an injection plunger 50 and an auto-loading flange mechanism 52, which is used as one exemplary design for connecting an injection plunger to a piston mechanism of a console. With this configuration, the end user will be able to minimize the amount of contact with the plunger, while still making the loading of the injection plunger onto the console relatively easy and secure. The injection device or catheter system can include an injection chamber that is in operative communication (i.e., directly or indirectly connected) with an injection or delivery lumen. That is, the injectate reservoir or source can be in operative communication with the injection plunger 50 and injection chamber to introduce or provide the fluid to the injection device or catheter system.

The injection plunger 50, which includes the auto-loading flange mechanism 52 adjacent one end, can be configured to feed through the inner diameter of an injection chamber. The flange portion 52 is configured to engage with, mate with, or otherwise abut or stop against, the end of a cylinder rod 58 that is provided with a piston mechanism 59 of a fluid injection console 60 (e.g., a console commercially available under the trade designation "Genesis" from American Medical Systems of Minnetonka, Minn.). That is, the flange portion 52, which is disposed generally adjacent to the proximal end of the plunger 50, will push up against a stop surface that is at or within the injection console 60 during loading of the plunger 50. This will stop the proximal end of the plunger 50 from moving further, thereby allowing the plunger 50 to lock into the piston mechanism 59 of the console 60. As such, a person assembling the components will not have to physically grasp the injection plunger 50 or manually push down in order to load the injection plunger 50 onto the injection console 60. Various other structural configurations are also contemplated for locking or engaging the plunger 50 with components of the console 60 to facilitate the auto-loading features described above.

Figure 7:
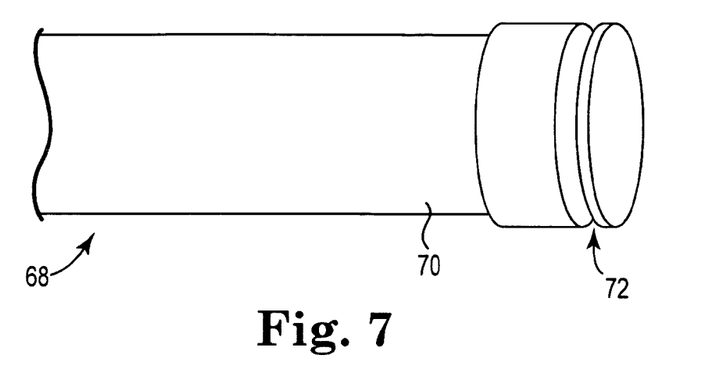
FIG. 7 is a perspective view of a distal end of an injection plunger having a shaft portion for sealing with an injection chamber.
Figure 8:
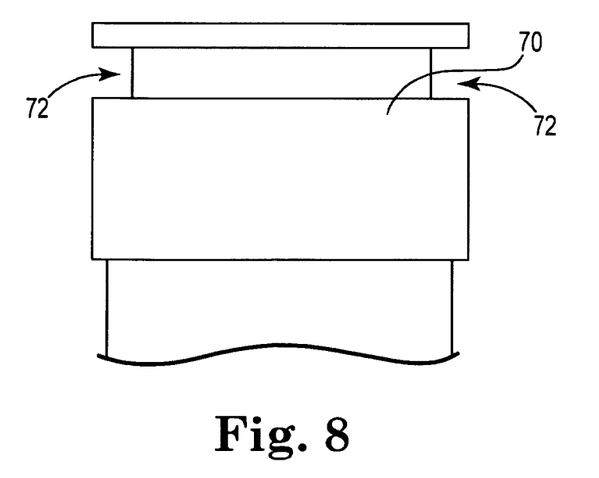
FIG. 8 is a front view of a distal end of the injection plunger of FIG. 7.

FIGS. 7 and 8 illustrate a distal end of an injection plunger that includes a shaft portion for sealing with an injection chamber. In particular, an exemplary injection plunger 68 is illustrated, which includes a shaft portion 70 configured to create a tight seal when in contact with the high-pressure zone of an injection chamber (e.g., a syringe). As shown, the shaft portion 70 includes a stepped or grooved area 72 that is adjacent to its distal end. This grooved area 72 can cooperate with an injection plunger o-ring (not shown), which is sized and shaped to fit securely within the grooved area 72. In this way, the plunger 68 can be configured so that only this portion of its length (e.g., the o-ring portion) is required to provide a tight seal within the injection chamber. This allows for more loose manufacturing tolerances for the remaining length of the shaft 70, since it will be spaced from the o-ring area and therefore will not come in contact with the high pressure area of the injection chamber. The shaft portion 70 of the plunger can be molded, machined, or otherwise formed to provide the desired tight tolerances proximate the grooved area 72, to thereby create a tight seal throughout each injection sequence.

Figure 9:
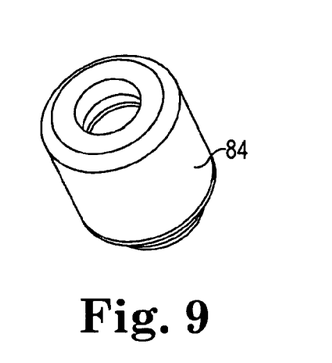
FIG. 9 is a perspective view of a quick-connect collar for attachment of an injection chamber and delivery tubing of the invention.
Figure 10:
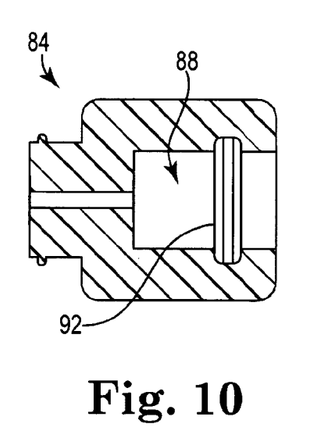
FIG. 10 is a cross-sectional side view of the quick-connect collar of FIG. 9.
Figure 11:
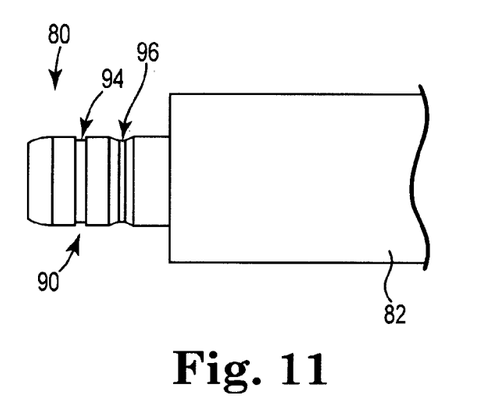
FIG. 11 is a side view of a distal end of an injection chamber that is connectable with the quick-connect collar of FIGS. 9 and 10.

As discussed above, the device tubing or delivery lumens of the systems of the invention are in operative communication with an injection chamber, such as a syringe. One exemplary physical manner of establishing this communication, in accordance with the invention, is via a quick connect mechanism, as is illustrated in FIGS. 9-11. In these Figures, a quick-connect mechanism 80 is shown for attaching the distal end of an injection chamber 82 and a delivery lumen, which also serves to provide fluid communication between the injection chamber 82 and the delivery lumen. In general, the quick connect mechanism comprises a collar 84 that is removably connectable to an extending feature or portion 90 of an injection chamber 82.

The proximal end of a delivery lumen of this embodiment can include a spring device that allows a collar on the delivery lumen to easily snap into place with a certain predetermined force when loading it onto the injection chamber and when removing the collar from the injection chamber. In particular, a spring device (e.g., a spring commercially available from Bal Seal Engineering, Inc. of Foothill Ranch, Calif.) is incorporated with a collar 84, which can be used for removable attachment between the collar and an extending feature or portion 90 of the injection chamber 82. The collar 84 includes a compliant cavity 88, which includes an enlarged portion for a spring 92. The extending feature or portion 90 of injection chamber 82 is adapted to mate with the collar 84, wherein the extending portion 90 can include a spring feature 96 that interacts or mates with the spring 92 when the devices are attached, and an o-ring groove 94 distal to the spring feature 96, which can be used with an o-ring in providing a fluid seal between the collar and the distal end of the injection chamber. In this way, the delivery lumen and collar 84 allow for removable and repeatable attachment of these components without degradation of the connection interface. The spring 92 within the cavity 88 can be customized or configured to hold certain desirable or predefined loading and unloading forces according to the particular system design requirements. Further, the use of an o-ring with the injection chamber 82 can provide a tight seal between the tubing and the injection chamber. In addition to the described and depicted seal and connection mechanisms, other devices and techniques known in the art for releasably sealing connecting components (e.g., injection chamber and tubing) can also be used.

Figure 12:
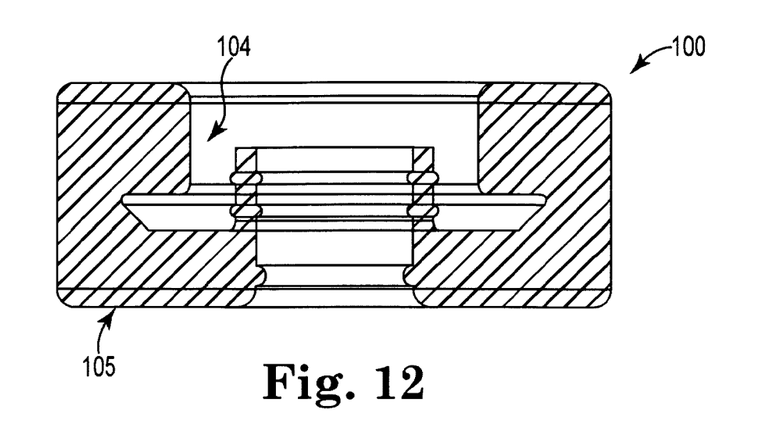
FIG. 12 is a cross-sectional front view of a retention gasket used for attachment between an injection chamber and a console, in accordance with the invention.
Figure 13:
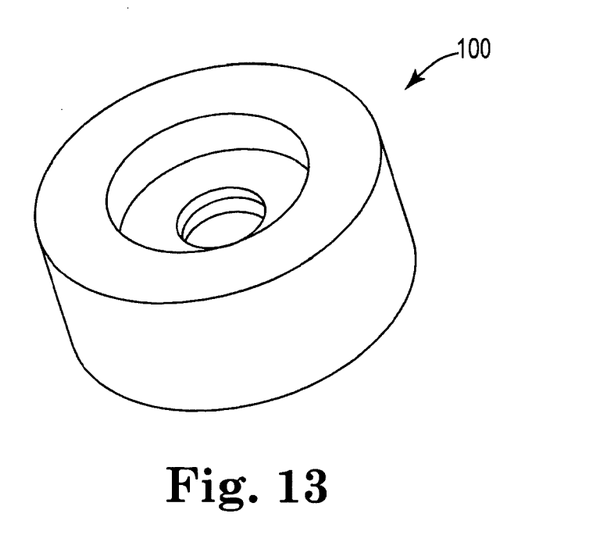
FIG. 13 is a perspective view of the retention gasket of FIG. 12.

FIGS. 12 and 13 illustrate an exemplary manner of creating a seal between an injection chamber and an injection plunger, as well as a means for attaching the injection chamber to an injection console. In particular, a retention gasket mechanism 100 is shown, which is positioned within an injection chamber, preferably in a relatively low-pressure area. The gasket mechanism 100 creates a desirable seal to reduce or eliminate fluid leakage during use of a fluid delivery system. The mechanism 100 is generally positionable intermediate an injection chamber and a console, and therefore generally includes a chamber receiving portion or space 104 and a console engagement portion or space 105. The chamber-receiving portion 104 can be sized and shaped to seal with and receive an end of an injection chamber, while the console engagement portion 105 (e.g., the outer diameter of the gasket) can be configured to tightly press into a cavity of the console. The outer diameter of the gasket mechanism can also be sized appropriately in order to mate with the injection console and aid in keeping the injection chamber and injection plunger in the correct position on the injection console during a procedure. This mechanism 100 thereby advantageously provides for an integrated sealing and attachment mechanism between the injection chamber and injection console. This mechanism 100 can be constructed from a wide variety of materials, including polymers, rubbers, and the like, wherein the materials can be at least somewhat flexible to accommodate for various spaces and tolerance gaps. Other known sealing and attachment devices, features, and techniques can also or alternatively be incorporated with the gasket mechanism 100, in accordance with the invention.

Figure 14:
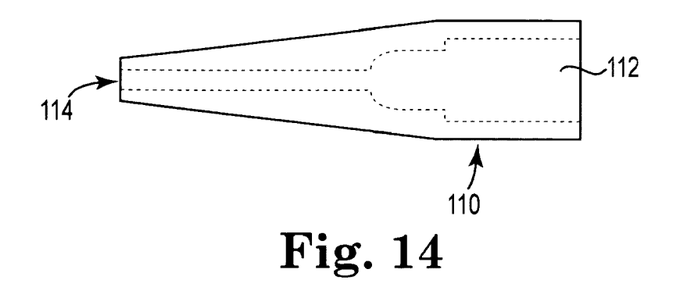
FIG. 14 is a front view of a distal end of a strain relief component for use at the transition area between the distal end of an injection chamber and the proximal end of an injection tube.
Figure 15:
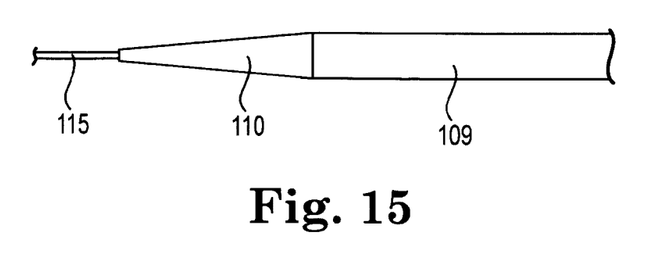
FIG. 15 is another front view of a distal end of a strain relief component, along with an associated injection tube and injection chamber.

In embodiments of the invention, the diameter at the distal end of an injection chamber can be significantly different than the diameter at the proximal end of an injection tubing or delivery lumen. To provide a smooth circumferential transition between a delivery lumen and an injection chamber of the systems of the invention, a tapered strain relief feature 110 can be provided, as is illustrated in FIGS. 14 and 15. The strain relief feature 110 can be tapered or cone-like in shape, and can include a cavity 112 at one end to receive the outer diameter of the distal end of an injection chamber 109, and a gradual or tapered end 114 to engage with or slide over the proximal end of a tubing 115. That is, the strain relief feature 110 is slideable over the tubing 115 and attaches to the distal end of the injection chamber 109, thereby providing support to the tubing 115 between the diameter transition of the injection chamber 109 and the tubing 115, both while the injection system is an use and when it is at rest. Some examples of how the strain relief feature 110 advantageously provides sufficient support to the tubing during use include situations when unintentional forces are placed on the tubing, when the user puts excessive force on the tubing, and when "whipping" forces are placed on the tubing. Further, the tapered end 114 can provide support to resist kinking during use. The shape, size, configuration, and materials for the strain relief feature 110 can vary widely, depending on the particular design and application requirements for the fluid delivery system, in accordance with the invention.

Figure 16:
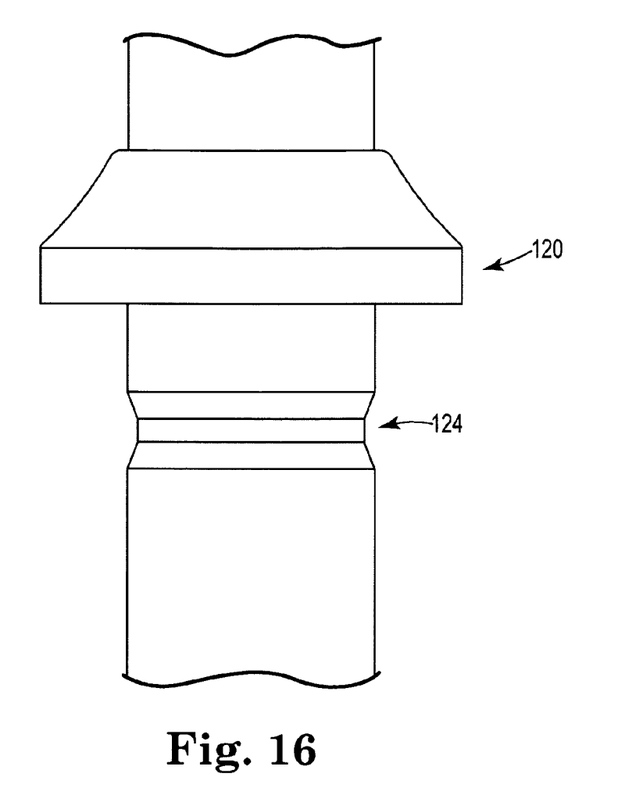
FIG. 16 is a front view of a connector for use in attaching a console to an injection plunger, in accordance with the invention.
Figure 17:
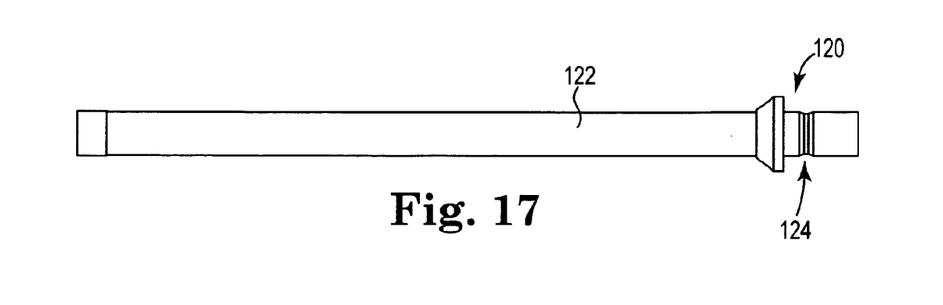
FIG. 17 is a front view of a plunger for use with the connector of FIG. 16.

FIGS. 16 and 17 illustrate a connector feature 120 of the invention, which is adapted to facilitate attachment between an injection plunger 122 and an injection console. The feature 120 is configured for easy connection between the respective components before or after a delivery procedure, and can also be capable of withstanding the speeds and pressures exerted on the system during the procedure. With this embodiment, a spring is used that allows the injection plunger to easily snap into place with a certain force when loading it onto the injection console and removing the injection chamber from the injection console with either the same force or as a specified loading force or a different removal force. The connector feature 120 can include a spring type configuration provided on the proximal end of the plunger 122. The plunger 122 can include a groove 124, which is adapted to receive a "snap" spring that is a part of the console with which it will engage. The size of the groove 124 and corresponding spring can vary depending on the particular insertion and retraction forces to which the connection will be subjected. One advantage of this configuration of the connector feature 120 is that it allows for repeated connection and disconnection of the components without degrading the connection interface between the plunger 122 and a corresponding console.

Figure 18:
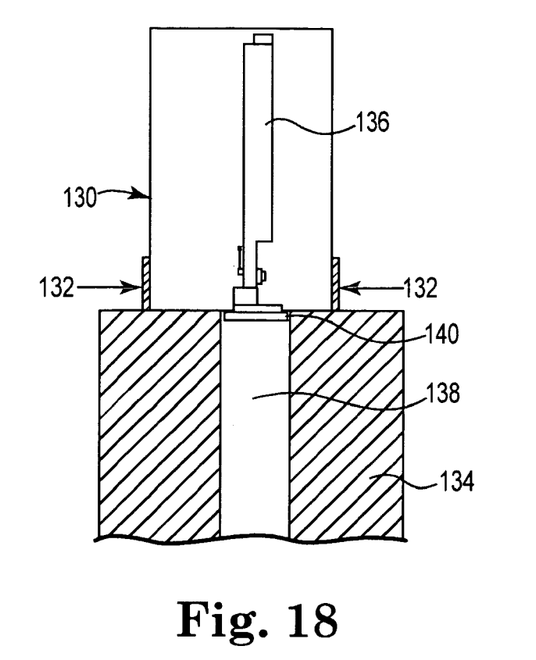
FIG. 18 is a front view of a sliding clamshell connection mechanism for attaching an injection chamber, injection plunger, and retention gasket to a console, in accordance with the invention.

FIG. 18 illustrates a sliding clamshell connection feature 130 in accordance with another aspect of the invention. Clamshell feature 130 is adapted to lock and align an injection chamber, injection plunger, and retention gasket assembly onto or with an injection console. In particular, a pair of clamshells 132 can be attached to a sliding mechanism on an injection console 134, wherein the clamshell pieces can initially start apart in a first home position. Then, the user can place an injection chamber 136, an injection plunger 138, and a retention gasket 140 into or onto the injection console 134, and then slide or move the clamshell pieces 132 together (e.g., manually, mechanically, or electronically) into a locked and aligned position. Locking the clamshell pieces 132 together will also lock and align the components in place for the procedure. As such, locking and aligning the components can be achieved in one motion, which thereby makes the system relatively easy to use. Various channels, injection cavities, medication/fluid reservoir adapters, and other features and structures can be included with one or more of the clamshell pieces 132, as desired. In addition, other structures, mechanisms, and techniques can be employed to facilitate the locking and alignment characteristics of the connection feature 130.

Figure 19:
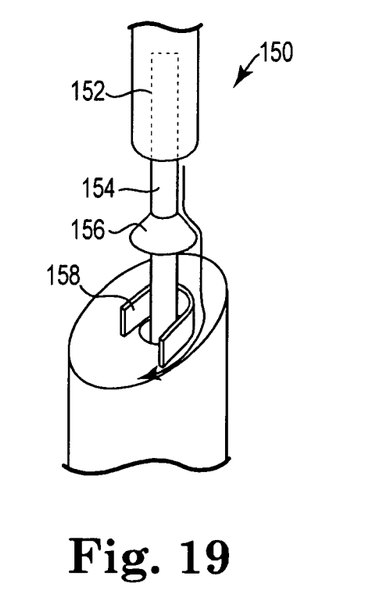
FIG. 19 is a perspective view of a leak management system for use with an injection lumen, in accordance with the invention.

In cases where an injection chamber and an associated plunger are oriented vertically within an injection console, injectate may potentially leak out of the injection chamber and run down the length of the plunger toward the console. In order to prevent the injectate from leaking into areas of the console or other components of its associated injectate delivery system, a leak management device 150 of the type illustrated in FIG. 19 can be incorporated into the system. In particular, an injectate delivery system can include a leak management device 150, which can be incorporated or provided with a component of the system, such as a delivery lumen. The device 150 can include a plunger 154, an umbrella flange 156, and a gutter 158. The plunger 154 is in operative communication with an injection chamber or lumen 152, and the umbrella flange 156 is positioned relative to the plunger 154 so that it flares outwardly relative to the plunger 154. This umbrella flange 156 can thereby divert fluids that leak from the chamber or lumen 152 along the plunger 154 to prevent or minimize the movement of fluids into the console or other potentially exposed openings in the system. In addition, the gutter 158 can be positioned as another manner of diverting fluids to prevent them from reaching a certain opening. The components of the leak management device 150 may be constructed of various materials, and can be either separately attached or integrally provided with certain components of the fluid delivery system. It is understood that both the umbrella flange 156 and gutter 158 can be provided in different configurations than shown to divert fluids. For example, an injection chamber can include more than one umbrella flange, and/or any of the flanges can be sized, shaped, angled, and/or otherwise configured differently than the tapered cone shape illustrated. For another example, the gutter 158 can include multiple components that are spaced from each other around a particular opening, such as a console opening, to direct fluid in a desired direction, and any provided gutters can be sized, shaped, angled, and/or otherwise configured differently than the gutter that is shown in FIG. 19.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A needleless fluid injection system comprising:
   an injection console;
   an injectate shaft in operative communication with the console and comprising an injection lumen extending from a proximal end to a distal end of the shaft, wherein the injection lumen is configured for carrying injectate under high pressure from the proximal end to the distal end of the shaft; and
   at least one injection orifice extending through a wall of the injectate shaft proximate the distal end of the shaft;
   wherein a distal end of the injectate shaft comprises a sealing cap that is at least partially compressed onto the injectate shaft, and wherein the sealing cap is tapered or cone-shaped to facilitate movement and placement of the injectate shaft within a patient.

2. The injection system of claim 1, wherein the sealing cap comprises an internal cavity.

3. The injection system of claim 2, wherein the internal cavity comprises an inner diameter that is at least slightly larger than an outer diameter of the injectate shaft.

4. The injection system of claim 2, wherein the internal cavity comprises a predetermined depth that is approximately equal to a predetermined length of the injectate shaft that will be positioned within the cavity.

5. The injection system of claim 1, wherein the sealing cap is adapted to receive an end portion of the injectate shaft, wherein the cap can withstand pressures greater than about 3000 psi.

6. The injection system of claim 5, wherein the sealing cap comprises a hollow portion for receiving the end portion of the injectate shaft.

7. A needleless fluid injection system comprising:
   an injection console comprising a cylinder rod positioned in an inner portion of the injection console;
   an injectate shaft in operative communication with the console and comprising an injection lumen extending from a proximal end to a distal end of the shaft;
   at least one injection orifice extending through a wall of the injection lumen proximate the distal end of the shaft; and
   an injection plunger comprising an extending flange portion proximate to its proximal end, wherein the injection plunger is positioned within the inner portion of the injection console, and wherein the flange portion is engageable with an end of the cylinder rod.

8. The injection system of claim 7, wherein the extending flange portion of the injection plunger is engageable with a portion of the injection console.

9. The injection system of claim 7, wherein the injection plunger further comprises at least one o-ring groove spaced from a distal end of the plunger.

10. The injection system of claim 9, further comprising an o-ring positioned in the o-ring groove.

11. A needleless fluid injection system comprising:
    an injection console;
    an injection chamber in operative communication with the console, the injection chamber comprising an extending portion extending from one end and comprising an o-ring groove;
    an injectate shaft in operative communication with the console and comprising an injection lumen extending from a proximal end to a distal end of the shaft;
    at least one injection orifice extending through a wall of the injection lumen proximate the distal end of the shaft, wherein the injection lumen is in operative communication with the injection chamber;
    an intermediate connector operatively connecting a distal end of the injection chamber to the injectate shaft, the intermediate connector comprising an internal cavity that is engageable with the extending portion of the injection chamber; and
    an o-ring positioned in the o-ring groove.

12. A needleless fluid injection system comprising:
   an injection console;
   an injection chamber in operative communication with the console, the injection chamber comprising an extending portion extending from one end and comprising a spring groove;
   an injectate shaft in operative communication with the console and comprising an injection lumen extending from a proximal end to a distal end of the shaft;
   at least one injection orifice extending through a wall of the injection lumen proximate the distal end of the shaft, wherein the injection lumen is in operative communication with the injection chamber;
   an intermediate connector operatively connecting a distal end of the injection chamber to the injectate shaft; and
   a spring positioned in the spring groove;
   wherein the intermediate connector comprises a spring cavity in operative engagement with the spring groove.

* * * * *